United States Patent [19]

Schlagheck et al.

[11] Patent Number: 5,808,303

[45] Date of Patent: Sep. 15, 1998

[54] INFRARED SCREENING AND INSPECTION SYSTEM

[75] Inventors: Jerry Schlagheck, West Chester, Ohio; Pierre Beaudry, Gatineau, Canada

[73] Assignee: Art Aerospace Research Technologies Inc., Ville St. Laurent, Canada

[21] Appl. No.: 790,451

[22] Filed: Jan. 29, 1997

[51] Int. Cl.⁶ .......................... G01N 21/88; G01N 25/72
[52] U.S. Cl. ...................... 250/330; 250/352; 250/358.1; 374/4; 374/124
[58] Field of Search .............................. 374/4, 6, 7, 124, 374/179; 250/330, 332, 358.1, 360.1, 352, 339.03, 339.04, 341.6

[56] References Cited

U.S. PATENT DOCUMENTS

| | | | |
|---|---|---|---|
| 3,803,413 | 4/1974 | Venzetti et al. | 250/338 |
| 4,998,582 | 3/1991 | Fudono et al. | 165/11.1 |
| 5,208,528 | 5/1993 | Quintard | 324/158 R |
| 5,250,809 | 10/1993 | Nakata . | |
| 5,294,198 | 3/1994 | Schlagheck . | |
| 5,594,249 | 1/1997 | Benefiel et al. | 250/339.03 |

FOREIGN PATENT DOCUMENTS

| | | | |
|---|---|---|---|
| 2015162 | 4/1990 | Canada . | |
| 5-67660 | 3/1993 | Japan | 374/6 |

*Primary Examiner*—Edward J. Glick
*Assistant Examiner*—Darren M. Jiron
*Attorney, Agent, or Firm*—George A. Seaby

[57] ABSTRACT

In general, the spatial resolution and repeatability of results using infrared detectors for examining printed circuit cards has been so poor that the devices have failed to achieve commercial success. These problems are overcome by a system including an isothermal enclosure for receiving a card to be tested, an infrared camera in the chamber defined by the enclosure, sensors for monitoring the temperature of the card and ambient temperature conditions in the chamber to derive signals indicative of the temperatures, and a computer connected to the camera and to the sensors for examining all signals to produce a three dimensional image of the sample, variations in the image from sample to sample being indicative of an anomaly in a sample.

7 Claims, 11 Drawing Sheets

INFRARED SCREENING AND INSPECTION SYSTEM

BACKGROUND OF THE INVENTION

1. Field of the Invention

This invention relates an infrared screening and inspection system.

Specifically, the invention relates to a system for inspecting circuit card assemblies using infrared technology. While the system was designed specifically for screening and inspecting circuit card assemblies, it will be appreciated that the system can be used for examining other workpieces.

2. Discussion of the Prior Art

Infrared technology has been studied, and indeed attempts have been made to use the technology for the inspection of circuit boards and other articles of manufacture. Examples of such attempts are described in Canadian Patent Application No. 2,015,162, filed by Robert Bishop on Apr. 23, 1990, and in U.S. Pat. No. 5,250,809, issued to S. Nakata et al on Oct. 5, 1993 and U.S. Pat. No. 5,294,198, issued to Jerry G. Schlaghack on Mar. 15, 1994.

For a variety of reasons, the use of infrared technology in the inspection of articles has an unfavorable reputation throughout the manufacturing industry. The reasons include the inability to acquire meaningful data and poor repeatability. In general, the spatial resolution of past infrared detectors was insufficient to permit the collection of useful data. Infrared is very susceptible to stray emissions and reflections, and because this condition was ignored, repeatability suffered. Moreover, circuit boards or cards from various manufacturers have different emissivity values. The differences are due to the differences in plastics or other materials used in the products, and is not necessarily related to color, because color has little effect in the infrared spectrum. In any event, with earlier systems repeatability from assembly to assembly was poor.

GENERAL DESCRIPTION OF THE INVENTION

The object of the present invention is to provide a solution to problems described above in the form of a relatively simple infrared inspection system, which is capable of acquiring data from a relatively small area, and which offers repeatability from one article to another.

Accordingly, the invention relates to an infrared inspection and detection system comprising:

(a) isothermal enclosure means defining an isothermal chamber for receiving a sample to be inspected;

(b) support means in said isothermal chamber for supporting a sample for inspection;

(c) infrared camera means in said isothermal chamber for monitoring infrared emissions from the sample and deriving a signal indicative of the temperature of all areas of the sample;

(d) sensor means in said isothermal chamber means for monitoring the temperature of said sample and ambient temperature conditions in said isothermal chamber, and deriving signals indicative of such temperatures; and (e) computer means connected to said camera means and to said sensor means for examining all signals to produce a three dimensional image of the sample, variations in the image from sample to sample being indicative of an anomaly in a sample.

BRIEF DESCRIPTION OF THE DRAWING

The invention is described below in greater detail with reference to the accompanying drawings, which illustrate a preferred embodiment of the invention, and wherein.

DESCRIPTION OF THE PREFERRED EMBODIMENT

Figure 1:
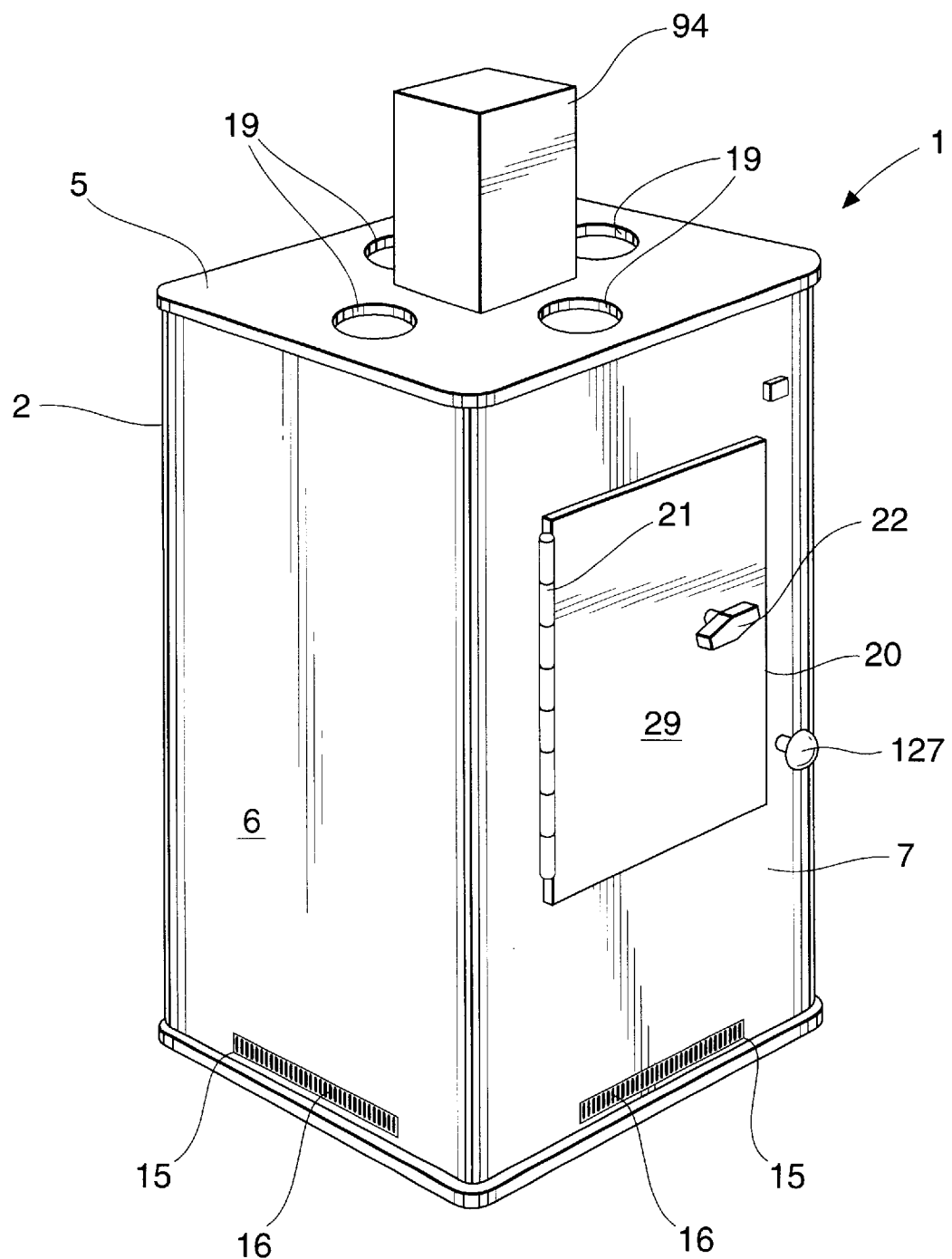
FIG. 1 is a perspective view of an isothermal enclosure for use in the apparatus of the present invention.
Figure 2:
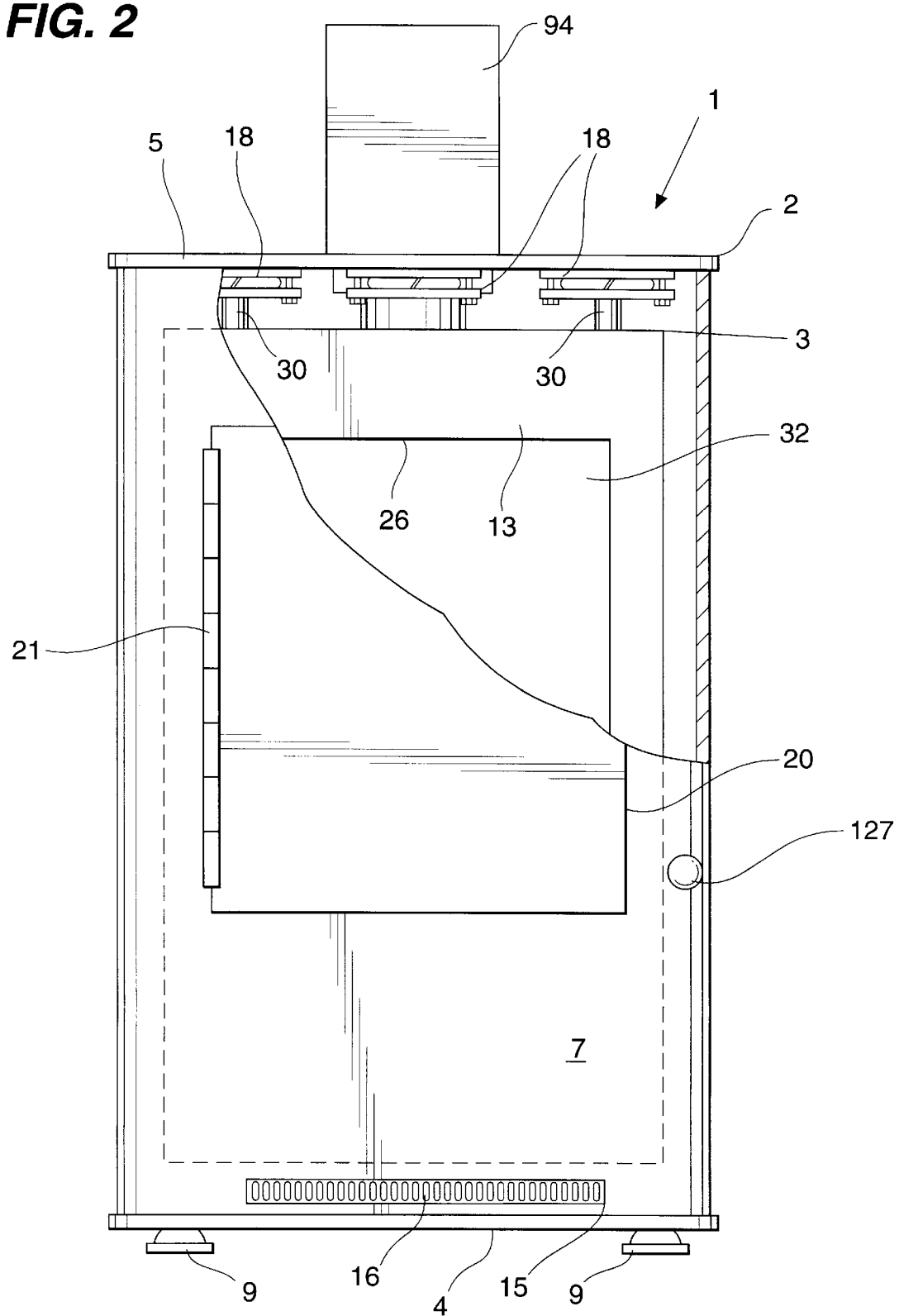
FIG. 2 is a partly sectioned front view of the enclosure of FIG. 1.
Figure 3:
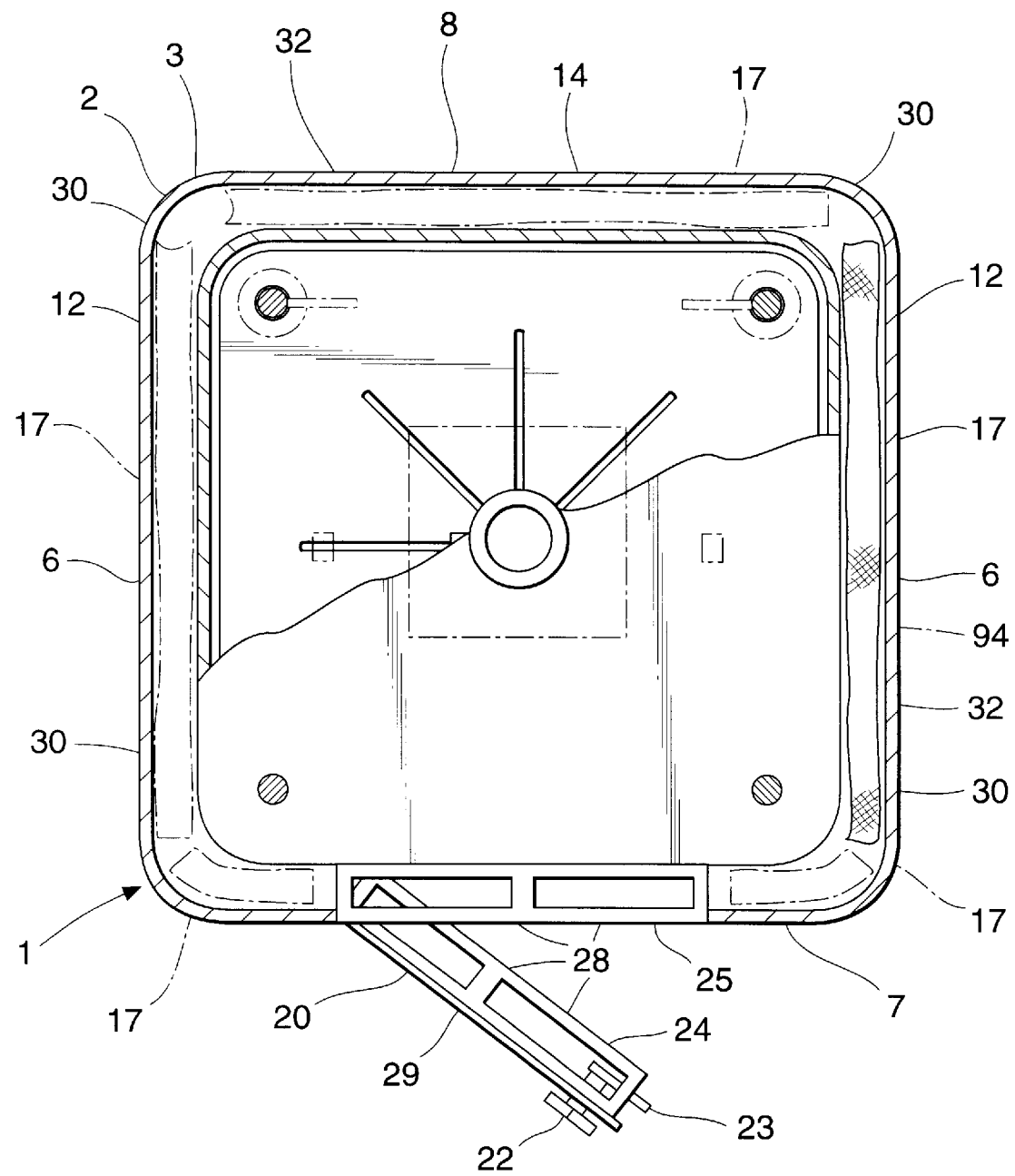
FIG. 3 is a cross section of the enclosure of FIGS. 1 and 2.

With reference to FIGS. 1 to 3, the isothermal enclosure used in the apparatus of the present invention which is generally indicated at 1 includes inner and outer housings 2 and 3, respectively, which are generally in the shape of rectangular parallelepipeds. The outer housing 2 is defined by a bottom wall 4, a top wall 5, side walls 6, a front wall 7 and a rear wall 8. Feet 9 are provided near the corners of the bottom wall 4 for supporting the housing 2 on a flat surface. The feet 9 are slightly flexible and have an inverted bowl-shape so that the housing is less susceptible to vibration than would otherwise be the case. Similarly, the inner housing 3 (FIGS. 2, 3, and 8 to 10, 12 and 13) is defined by a bottom wall 10, a top wall 11, side walls 12, a front wall 13 and a rear wall 14.

Vent slots 15 are provided near the bottom of the side walls 6 and the front wall 7 of the outer housing 2, permitting the circulation of air between the inner and outer housings 2 and 3, respectively. The slots 15 are partially closed by grills 16 mounted in the slots. Heat sinks in the form of steel wool mats 17 (FIG. 3) are provided between the side and end walls of the outer and inner housings 2 and 3, depending upon the characteristics of the target printed circuit cards. Heat is removed from the area between the housings 2 and 3 by four fans 18 (FIG. 2) mounted in circular openings 19 (FIG. 1) in the top wall 5 of the outer housing 2. Access to the enclosure 1 is gained through a door 20 in the front wall 7. The door 20 is connected to the front wall 7 by a piano hinge 21 on one side of the door. A knob 22 and a rotatable latch 23 (FIG. 3) are provided on the other side of the door 20. As best shown in FIG. 3, the door 20 includes a frame 24, which enters a second frame 25 extending between the outer housing 1 and the sides of an opening 26 (FIG. 2) in the front wall 13 of the inner housing 3. The frames 24 and 25 have longitudinally extending passages 28 which are aligned when the door 20 is closed to promote airflow between the housings 2 and 3. A rectangular panel 29 defines the outer skin of the door 20.

Figure 4:
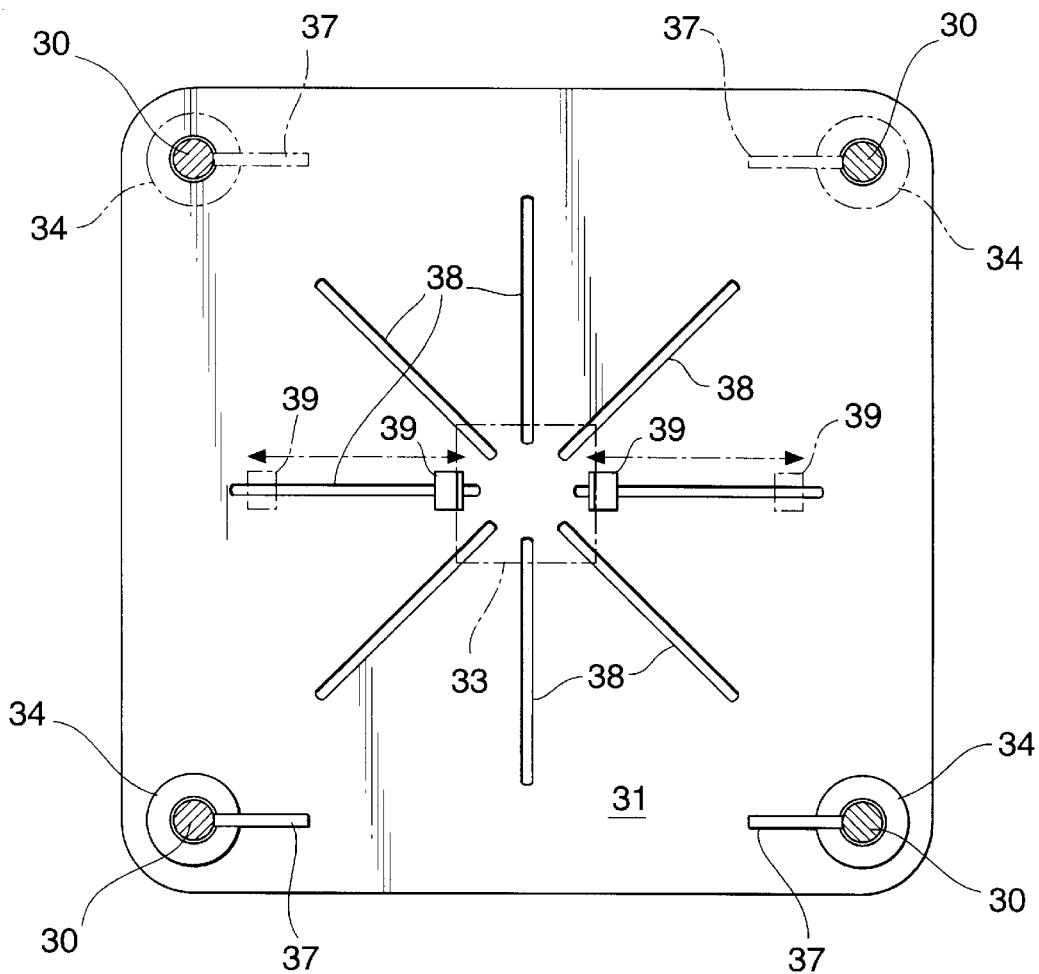
FIG. 4 is a top view of a printed circuit card support plate used in the enclosure of FIGS. 1 to 3.
Figure 5:
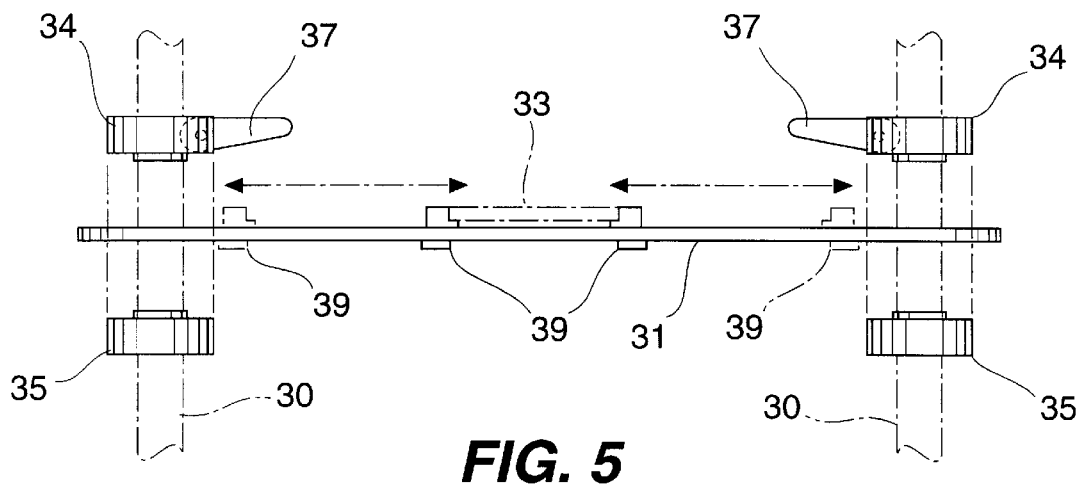
FIG. 5 is a side view of bushings and the sample support plate.

Four rods 30 in the outer housing 2 extend through the inner housing 3 near the corners thereof for mounting the inner housing in the outer housing. The rods 30 extend form the bottom wall 4 to the top wall 5 of the outer housing 2, passing completely through the inner housing 3. The rods 30 slidably support a sample receiving plate 31 in an isothermal chamber 32 in the inner housing 3. In this case, the sample is a printed circuit board or card 33 (FIGS. 4 and 5) to be tested for defects. The plate 31, which is generally rectangular, is formed of Bakelite (a trademark for various phenolformaldehyde, polystyrene and urea-formaldehyde resins). Bushings 34 and 35 formed of plastic (e.g. Telfon—a trade mark for polytetrafluoroethylene) are mounted in each corner of the plate 31 for slidably supporting the latter on the rods 30. Cam-type latches 37 are provided on the bushing 34 for releasably locking the plate 31 in one position on the rods 30.

Figure 6:
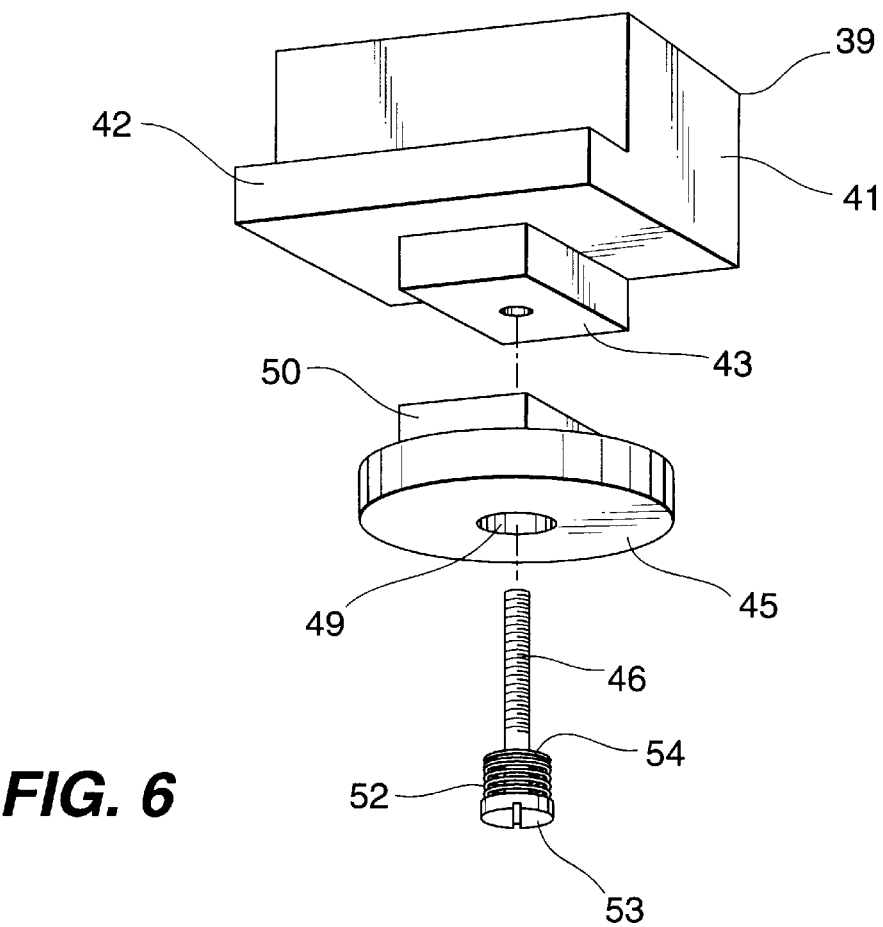
FIG. 6 is an exploded, isometric view of a sample support bracket used in the system of the present invention.
Figure 7:
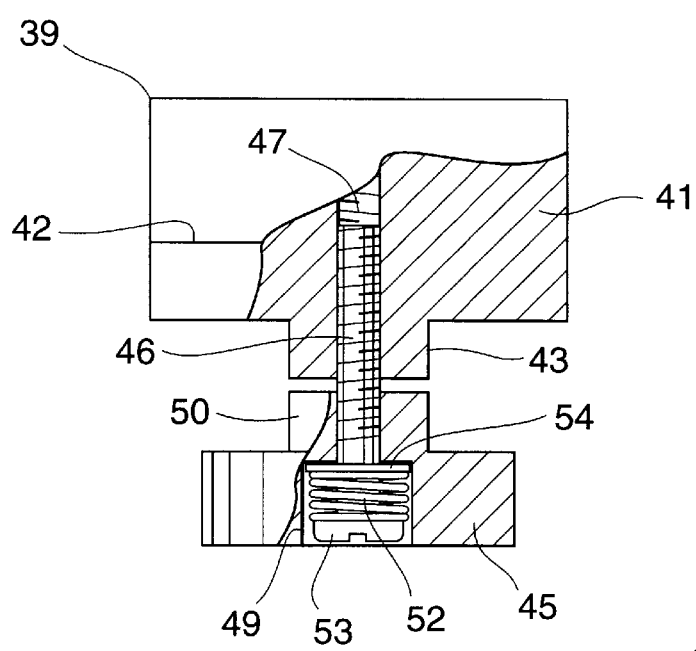
FIG. 7 is a partly sectioned front view of the bracket of FIG. 6.

Radially extending slots 38 in the plate 31 are designed to receive brackets or stops 39 for positively positioning a printed circuit card 33 on the plate 31. The use of a plurality of slots 38 permits the positioning of circuit cards 33 having a variety of dimensions and shapes, e.g. rectangular or circular on the plate 31. Referring to FIGS. 6 and 7, each bracket 39 includes a top block 41 with a ledge 42 extending outwardly from the bottom end of the front thereof for supporting one edge of the a printed circuit card 33. A projection or slide 43 extends downwardly from the bottom of the block 41 into a slot 38 in the plate 31. A disc-shaped foot 45 is mounted beneath the plate 31 using a screw 46, which extends into a threaded bore 47 in the block 41. The screw 46 is countersunk in a cylindrical recess 49 in the foot 45, and extends upwardly through a rectangular projection or slide 50 into the projection 43. Thus, the slides 43 and 50 oppose each other in the slot 38. A helical spring 52 is mounted on the screw 46. The spring 52 is sandwiched between the head 53 of the screw 46 and a washer 54 on the screw at the top end of the recess 49. With this arrangement, the foot 45 can be pulled downwardly against the bias of the spring 52, and the bracket 39 slid along the slot 38 to change the position of the brackets 39.

In use, a printed circuit card 33 is mounted on a plurality of brackets 39 by suitable positioning of the brackets in the slots 38. The vertical location of the plate 31 is adjusted in the isothermal chamber 32 using the cam latches 37. When the latches 37 are released, the plate 31 can be slid vertically along the rods 30 to the desired location. The latches are re-set to lock the plate 31 in position.

A second embodiment is illustrated in FIGS. 8 to 13. Wherever possible in FIGS. 8 to 13, the same reference numerals have been used to identify elements identical to or similar to elements illustrated in FIGS. 1 to 3.

The second embodiment of the isothermal enclosure includes outer and inner housings 2 and 3, respectively. The housings are assembled using a hollow, extended aluminum corner post generally indicated at 60. The corner post 60 includes outer and inner arcuate walls 61 and 62, respectively interconnected by sides 64 and a central web 65. The sides 64 include L-shaped ends 66 defining longitudinally extending grooves 67 for receiving the side and end walls of the outer and inner housings 2 and 3. The web 65 includes a pair of enlarged rectangular areas or bars 69 containing passages 70 and 71 therethrough for receiving screws (now shown).

Figure 9:
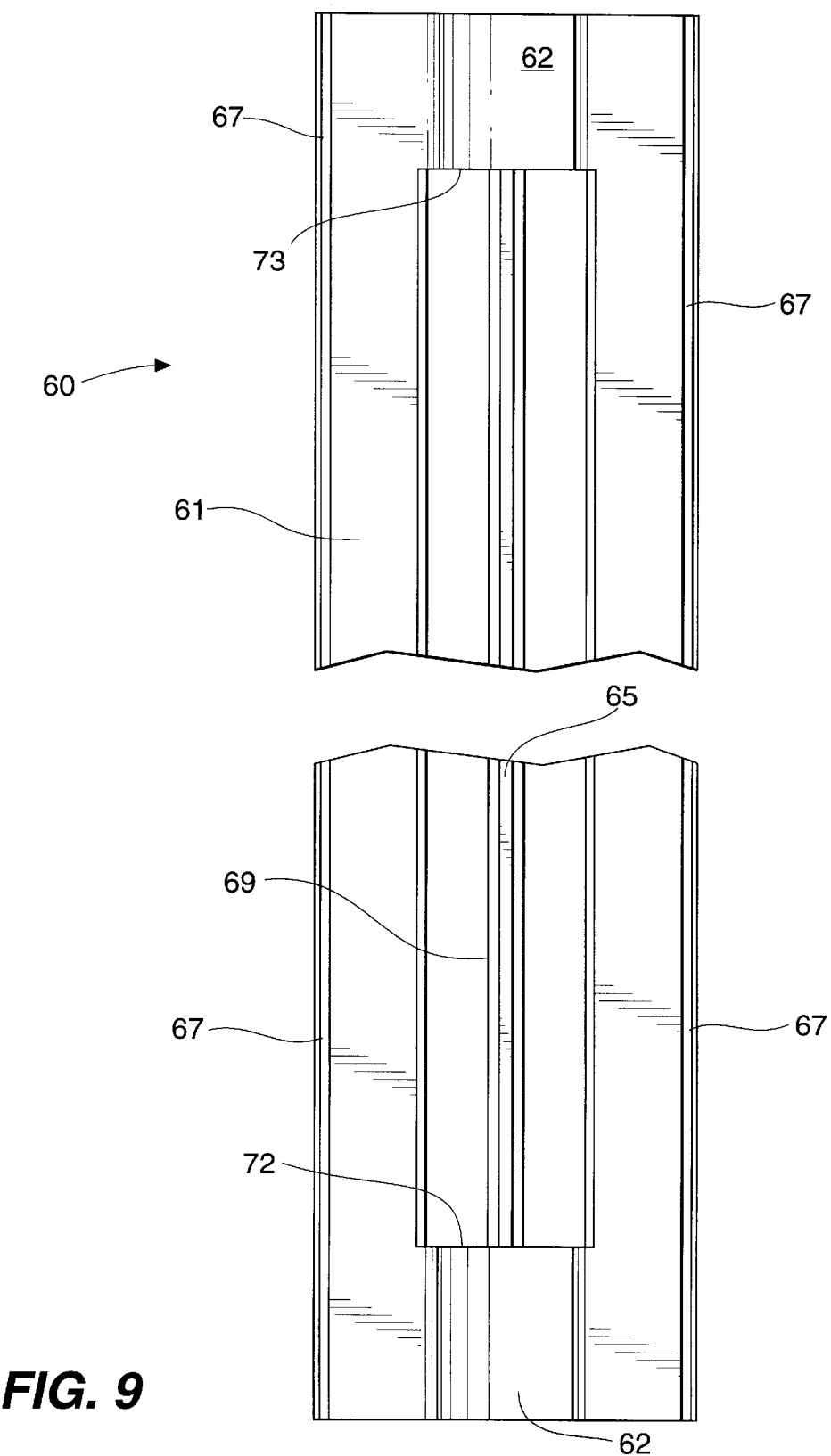
FIG. 9 is a front view of a corner post used in the isothermal enclosure of FIG. 8.
Figure 10:
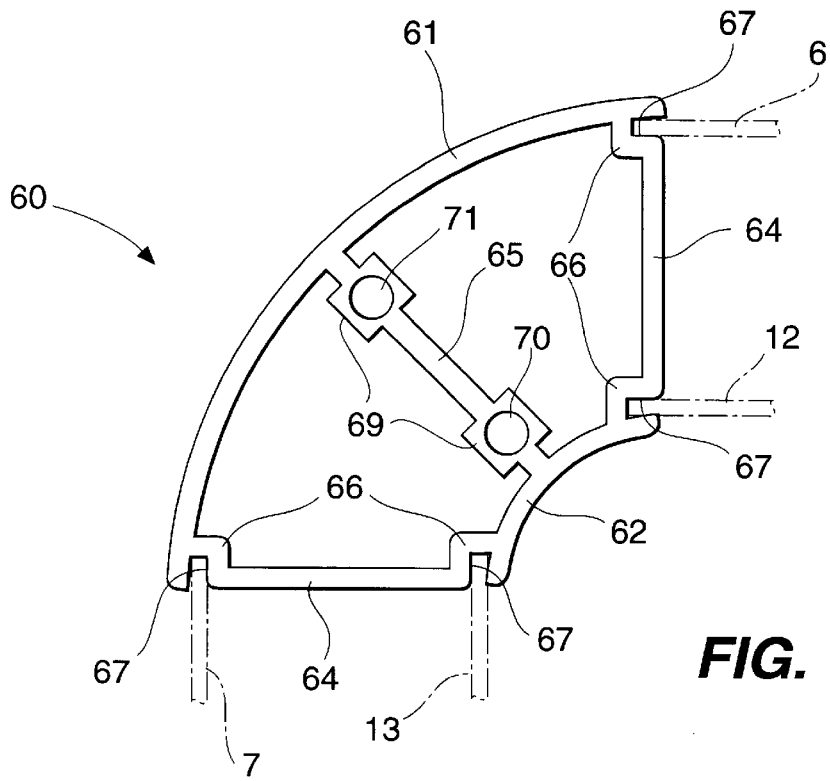
FIG. 10 is a top view of the post of FIG. 9.
Figure 11:
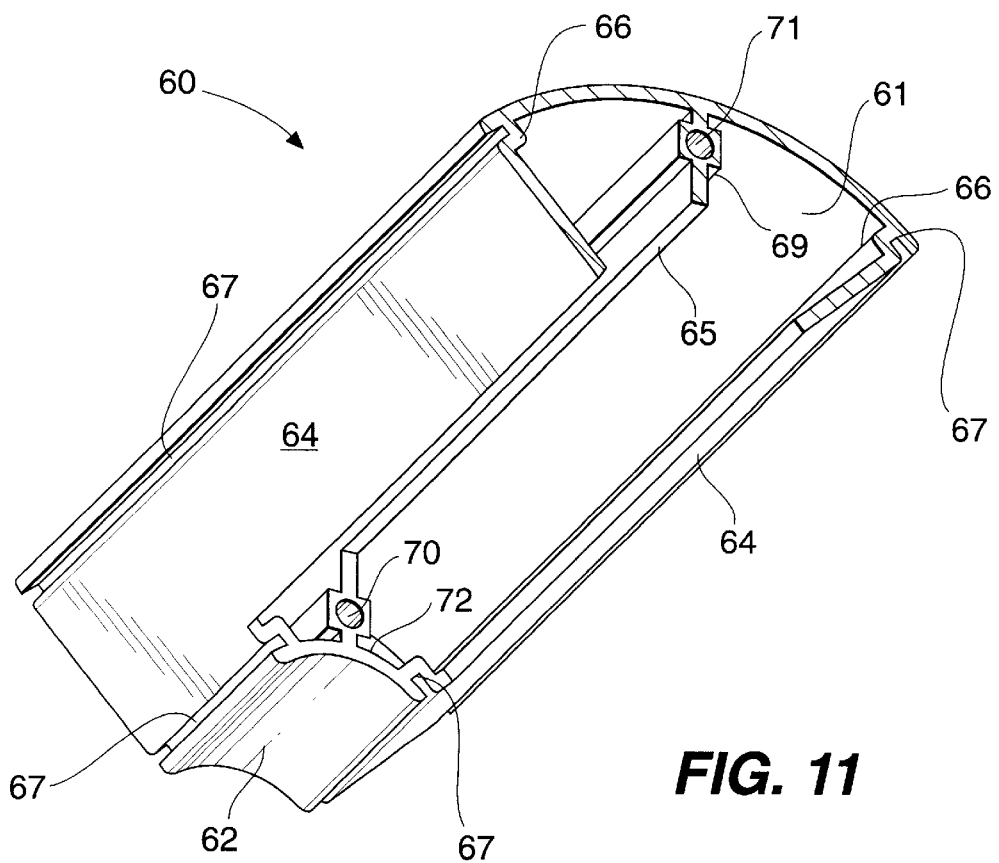
FIG. 11 is an isometric view of one end of the post of FIGS. 9 and 10.

As best shown in FIGS. 9 and 11, the inner side of the corner post 60 is recessed, i.e. the inner wall 62 and a portion of the web 65 attached thereto are cut away to leave a bottom ledge 72 and a top shoulder 73. The corners of the bottom wall 10 of the inner housing 3 are slide onto the ledges 72 of four corner posts 60 and connected thereto by screws (not shown) extending through such bottom wall into the innermost passage 70 in the post 60. Similarly, the corners of the top wall 11 of the inner housing are placed against the shoulders 73 of four corner posts 60, and secured thereto by screws extending through the top wall into the innermost passage 70.

Panels defining the side and end walls of the housings 2 and 3 are placed in the appropriate grooves 67. The top and bottom walls of the outer housing 2 are connected to the corner posts 60 using screws (not shown) which enter the outermost passages 71 in the extrusion.

Figure 8:
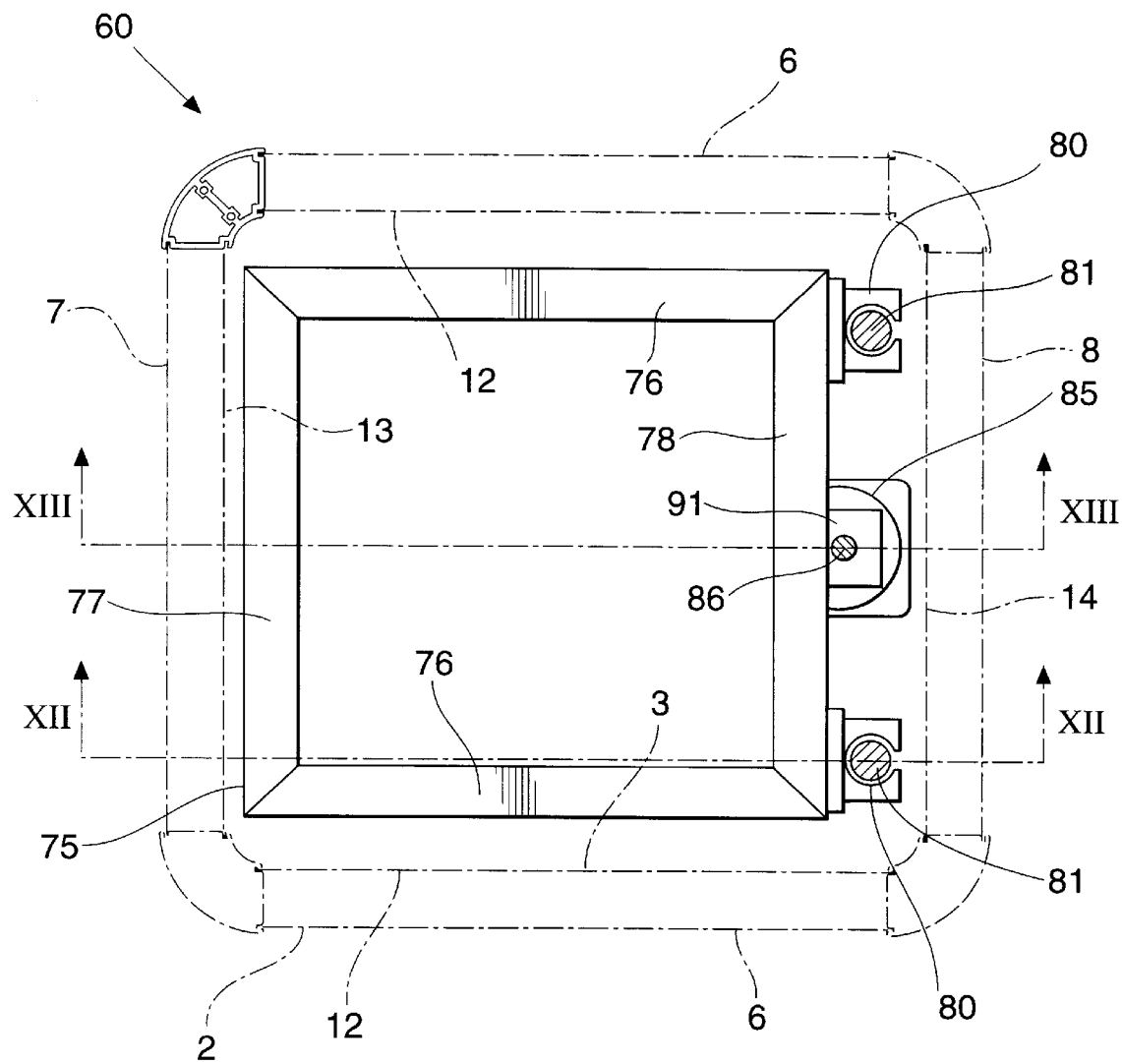
FIG. 8 is a cross-sectional view of a second embodiment of an isothermal enclosure for use in the apparatus of the present invention.
Figure 13:
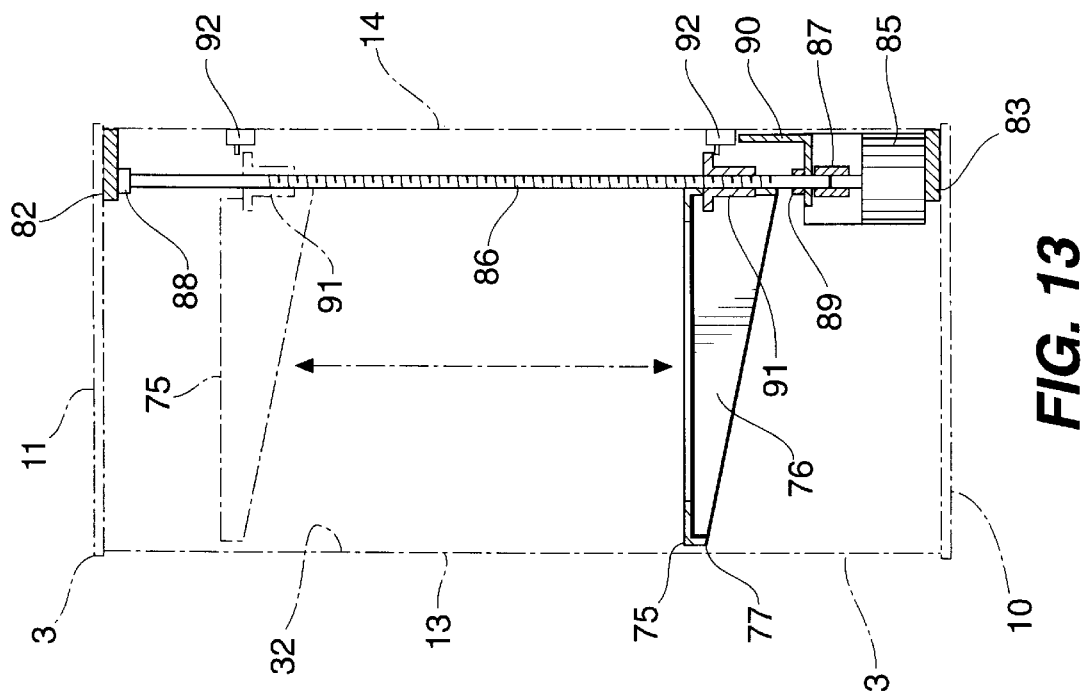
FIG. 13 is a cross section taken generally along line XIII–XIII of FIG. 8.
Figure 12:
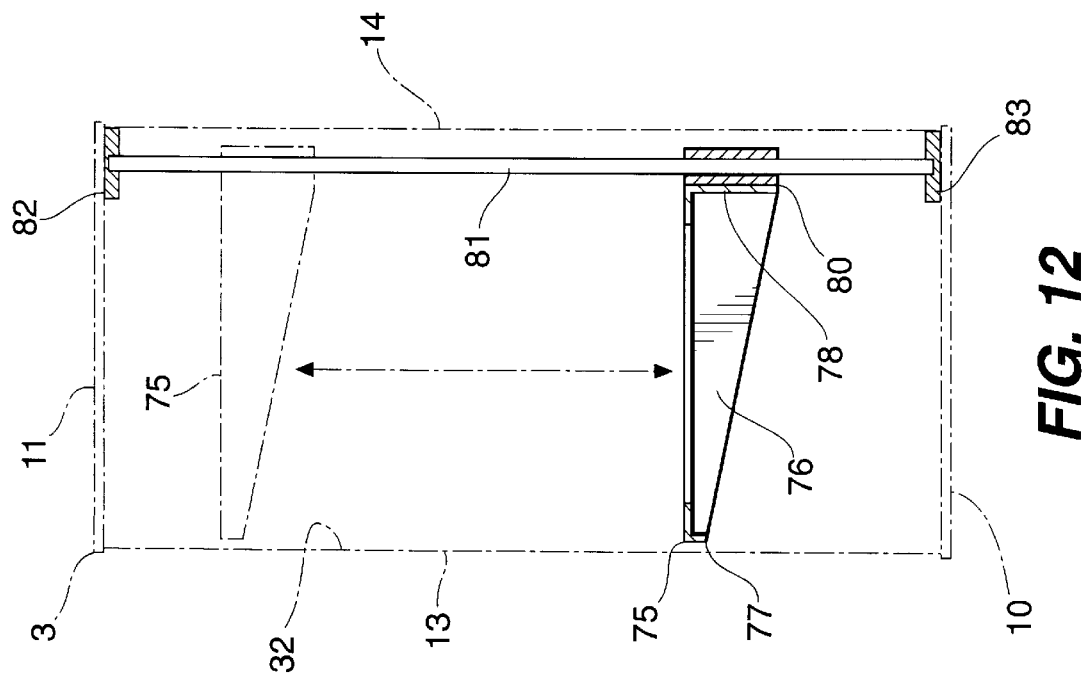
FIG. 12 is a cross section taken generally along line XII–XII of FIG. 8.

Referring to FIGS. 8, 12 and 13, in the second embodiment of the isothermal enclosure, the circuit card holder is an open rectangular frame 75 defined by sides 76, and front and rear ends 77 and 78, respectively. A pair of linear bearings 80 are provided on the rear end 78 of the frame 75 for slidably mounting the frame on a pair of tracks defined by rods 81 extending between plates 82 and 83 at the top and bottom, respectively of the inner housing 3.

The frame 75 is moved vertically on the rods 81 by means of a reversible motor 85 at the bottom center of the bottom plate 83. The motor 85 is connected to a threaded shaft 86 by a coupler 87. The shaft 86 is supported by thrust bearings 88 and 89 mounted on the top plate 82 and an angle bracket 90 near the bottom of the inner housing 3. The shaft 86 extends through an internally threaded sleeve 91 on the center of the rear end 78 of the frame 75. When the motor 85 is actuated, the shaft 86 is rotated to move the frame between the lower position illustrated in solid lines and the upper position illustrated in phantom in FIG. 13. Vertical movement of the frame 75 is limited by a pair of limit switches 92 mounted on the rear wall 14 of the inner housing 3. Thus, the frame 75 and the card 33 carried thereby can be precisely located in the isothermal chamber 32.

With the printed circuit card 33 positioned in the chamber 32, the card is ready for inspection to determine whether it has any defects. For such purpose, an infrared camera or radiometer 94 is mounted on the center of the top wall of the outer housing 2. The camera 94 extends through the space between the top walls of the outer and inner housings 2 and 3, respectively into the top center of the isothermal chamber 32. The camera 94 is in fact an infrared, focal plane array radiometric imager. A suitable device is the IRRIS-256S® available from Cincinnati Electronics Corporation, Mason, Ohio. The camera 94 provides a temperature signal which is fed to the control circuit of the present invention.

Figure 14:
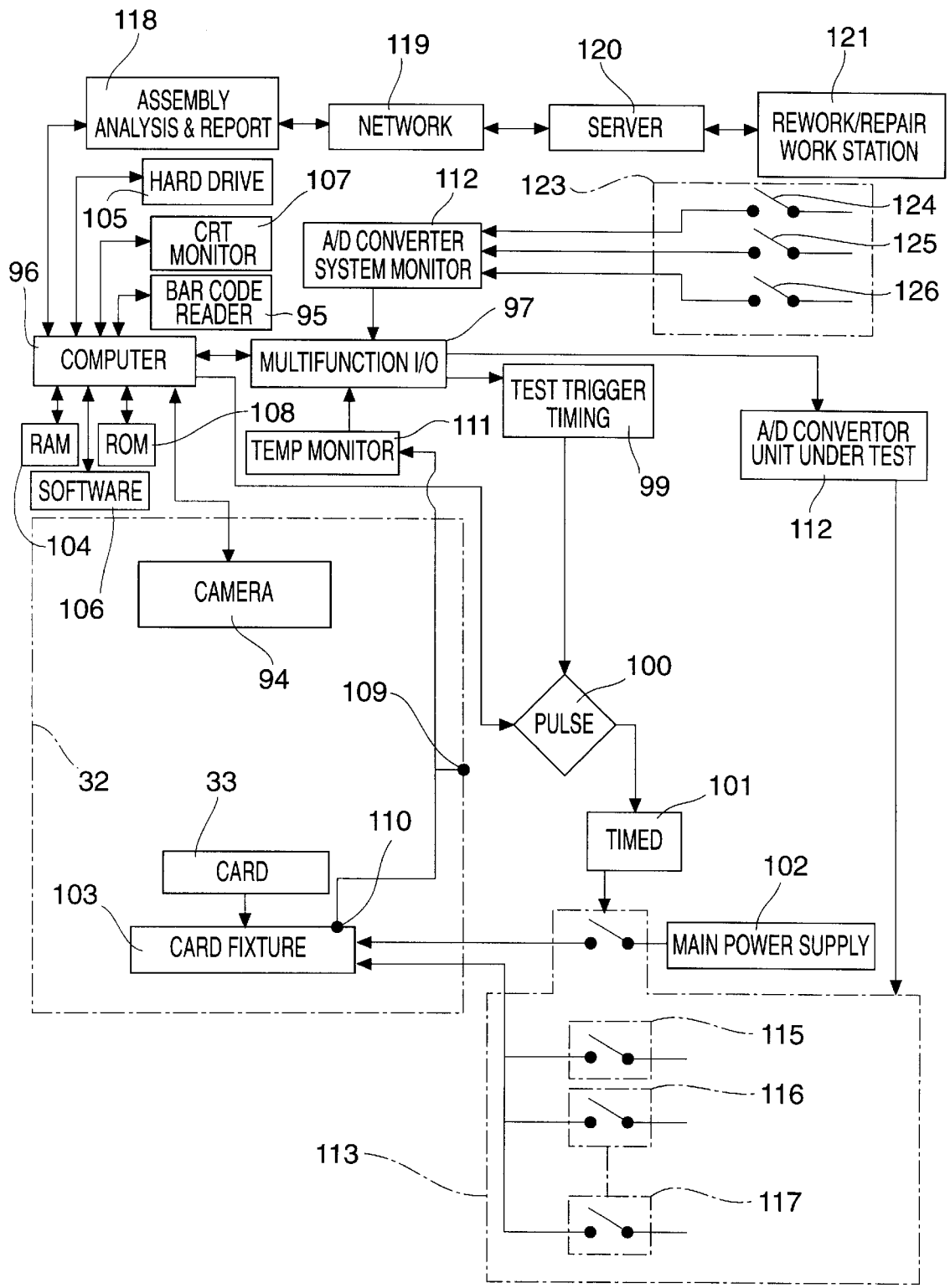
FIG. 14 is a schematic block diagram of a control circuit used in the system of the present invention.

Referring to FIG. 14, before placing a unit under test 33 (a printed circuit card) in the isothermal chamber 32, the card is scanned by a bar code reader 95. The reader 95 acquires the necessary information, namely board type, model number and other parameters which are used to set up the correct testing sequence. This information is fed to a main computer 96 along with signals from the camera 94.

The computer 96 initiates testing by sending digital signals to a multi-function I/O assembly 97. The first signal 99 is a test or board safety signal. The signal is pulsed at 100 and a timed event 101 occurs. The timed event 101 closes a main power support relay 102 and supplies voltage pulses to the unit under test 33 via a unit under test fixture 103 (at the plate 31 or frame 75). The pulses last for a period of less than 30 msec. Thus, this pre-test assembly provides main power to the system in a pulsing manner. At this point, the system is searching for any abnormal thermal reading circuits. If a short is detected, the test is aborted and the user is alerted to avoid harming the system.

The pulsed power acquired by the camera 94 and passed to the computer 96 for processing is stored in a random access memory (RAM )104 in an array and then transferred to the hard drive 105 for post processing using software 106 and display on a CRT 107. The computer 96 is also responsive to information stored in a read-only memory (ROM) 108. During processing, the computer 96 acquires ambient data via thermocouples 109 and 110 connected to a wall of the isothermal chamber and to unit under test fixture 103, respectively. The temperature measurements are processed by a temperature monitor assembly 111. These elements ensure that the system is constantly aware of any variations in ambient temperature. The constant monitoring of the temperature ensures that the heat in the chamber 32 and of the card fixture 103 do not rise to the point where the software algorithms cannot correct for thermal changes.

If no anomaly is observed, the computer 96 will initiate inspection of the card 33. The computer 96 will acquire six ambient card images (no power) and store the images in the RAM 104. The computer 96 will then initiate a full sequence of card tests providing various voltages or required signals via an A/D converter 112. The system provides various voltages via a breakout box 113 incorporating relays 115, 116 and 117. The signals applied are various voltages or signals required to stimulate the assembly to a fully functional condition. During this timed event, the computer 96 acquires data at specific intervals and stores the data in the RAM 104. At each point that the computer 96 acquires data in a minimum of three arrays. The array of data is the thermal value of each element of the camera or radiometer 94. The three arrays are averaged to eliminate noise. Upon completion of this cycle of operation, the computer 96 turns off the interlock power and/or signals to the card 33.

Software functions and algorithms are then performed on the arrays to determine the condition of the unit under test or card 33. The results of the data are compiled into analysis and report 118 and sent via network 119 and server 120. The server data can then be acquired at any rework/repair workstation 121 either by scanning a card via the bar code reader 95 or manually entering a model and serial number.

Power for the various elements described above comes from a main source, i.e. a 120 volt AC line via switches 123. The switches 123 include a main power switch 124, an interlock switch 125 and an emergency switch 126. The interlock switch 125 is located on the door 20 and will trip the main power if the door is opened. The emergency switch 126 is operated by a user operated pushbutton 127 (FIGS. 1 and 2) on the front wall of the outer housing 2 beside the door 20. The switch 126 is an emergency kill switch for operator safety. At any time, the operator can hit the button 127 and kill all power to the mechanical section, including the fans, etc.

In more general terms, the operation of the system is as follows. An operator applies power to the system by closing the main power switch 124. Thus, power is applied to all of the apparatus including the infrared camera 94, the fans 18, the bed of nails fixture 103 and the computer analysis system. After the system has been actuated, the system goes into standby for a period of ten minutes which allows the camera 94 and the isothermal chamber 32 to be properly conditioned prior to the start of testing. When the operator opens the inspection door 20, the interlock switch 125 removes power from the bed of nail fixtures 103 and shuts down all of the fans 18. The operator then places a circuit card 33 on the plate 31 or the frame 75. Alignment of the card with the fixture 103 and the camera 94 is achieved using the brackets 39 or tooling holes in the card and tooling pins (not shown) on the frame 75. The operator closes the door, whereby the interlocks are sensed by the computer 96 and the user can then initiate inspection. Upon completion, the computer 96 alerts the user that the test has been completed and that the card 33 can be removed and a new one inserted.

Figure 15:
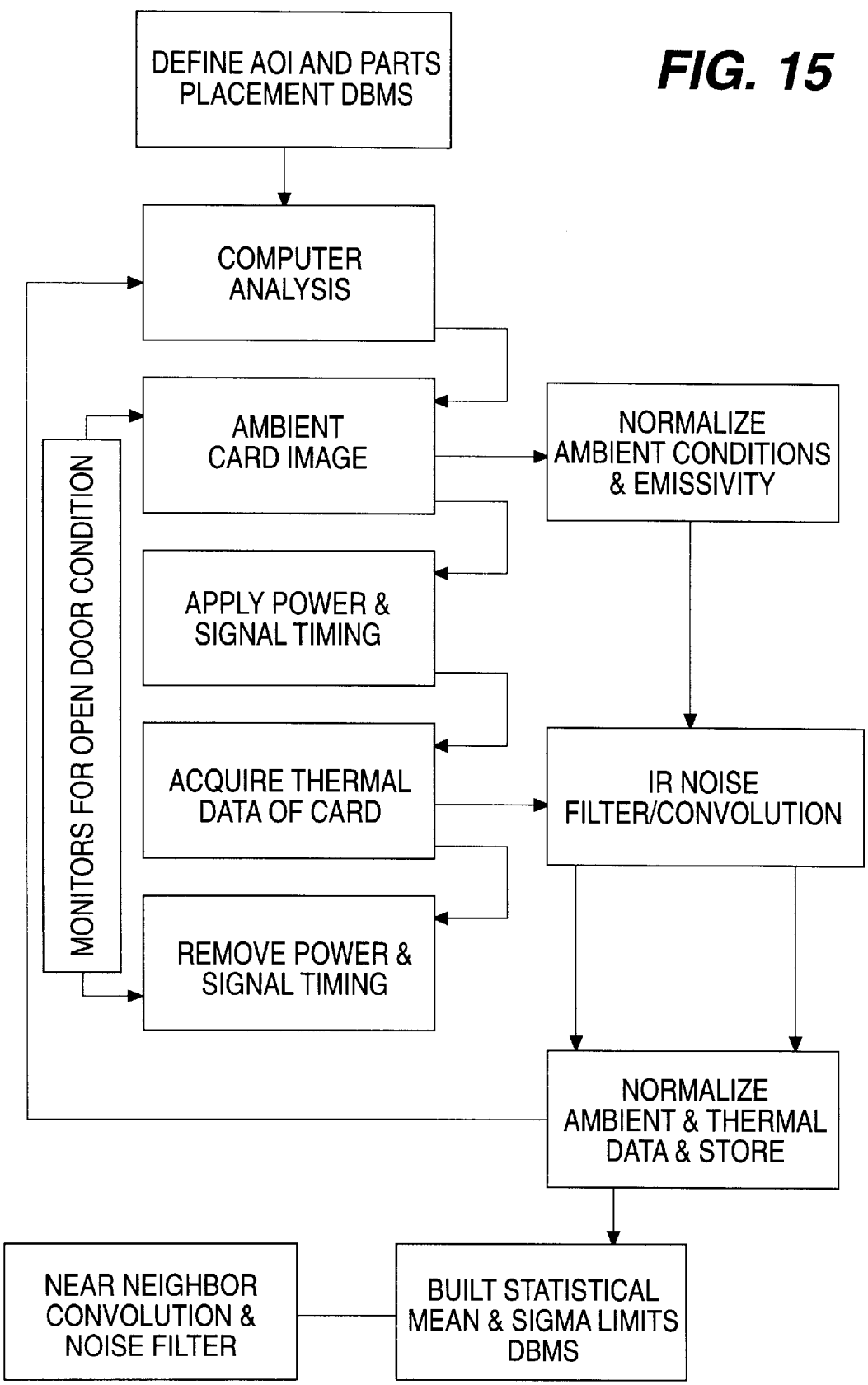
FIG. 15 is a schematic block diagram illustrating the operation of the circuit of FIG. 14.

As illustrated schematically in FIG. 15, the software used with the control circuit operates as follows:

The operator first defines a parts placement and general area of interest in a database management system (defined AOI and parts placement DBMS). This is accomplished by viewing an image of the circuit card 33 on a CRT 107, and drawing a box around each device that is to be screened/ inspected. The operation of drawing the box is by placing a mouse at coordinates at X1 and Y1 and holding the mouse button down until the box surrounds the card reaching position X2, Y2. Upon release, the mouse button user is prompted to enter the card ID and other user optional data. Each card selection and identification are logged to a specific board type DBMS and can be modified at any time by the operator. Once the DBMS has been defined, the operator will define the I/O sequences that are to be turned on or off at user specific times, in 1/60 of a second. Also to be defined are the overall duration that power is to be applied and the intervals for the camera 94 to acquire data. These steps complete the initial setup of the specific circuit card database management system. The next step is to build a standard database for the card 33. The card 33 is loaded and an ambient image is acquired. The image is then normalized and scanned for varying emissivity values, which are stored in the hard drive. After the image has been acquired and stored, the computer 96 will initiate the testing/screening process. The computer 96 will acquire images at specific intervals and store the raw data on a disc. At the completion of this sequence, the computer turnoff power and signals will alert the user to remove the card and insert a new one.

The computer 96 will post process the newly acquired data and perform an IR noise reduction rank filters and thermal convolutions rank filter, and store the data. After a minimum of twenty assemblies have been run through the process, the user will invoke a build function. During this process the computer 96 will generate a mean and upper and lower control limits. Newly acquired data images are compared to the statistical database management system (DBMS) and a Delta analysis is performed.

During analysis, the computer 96 will analyze each screen and IR element pixel and perform an algebraic subtraction of the data. During this process noise can be introduced into the system. To eliminate the noise, a near circular neighbor convolution and noise filter is applied and any erroneous pixels are normalized to their nearest circular neighbor. The computer then performs an overall sigma analysis and if any cards are found to be out of tolerance, the system will indicate either PASS or FAIL on the monitor 107. If failed, the image will undergo another analysis to identify the card and/or the location of the anomaly. A complete report is generated, the report including card identification, e.g. model number, serial number, revision number, operator ID, data and condition, i.e. elements which are out of tolerance.

We claim:

1. An infrared inspection and detection system comprising:
   (a) isothermal enclosure means, said isothermal enclosure means including:
      (i) outer housing means;
      (ii) inner housing means located in and spaced apart from said outer housing means, said inner housing means defining an isothermal chamber for receiving a sample to be inspected; and
      (iii) air conditioning means for removing heat from between said outer and inner housing means;
   (b) support means in said isothermal chamber for supporting a sample for inspection;
   (c) infrared camera means in said isothermal chamber for monitoring infrared emissions from the sample and deriving a signal indicative of the temperature of all areas of the sample;
   (d) sensor means in said isothermal chamber for monitoring the temperature of said sample and ambient temperature conditions in said isothermal chamber, and deriving signals indicative of such temperatures; and
   (e) computer means connected to said camera means and to said sensor means for examining all signals to produce a three dimensional image of the sample, variations in the image from sample to sample being indicative of an anomaly in a sample.

2. The system of claim 1, wherein said air conditioning means includes vent means in the top and bottom of said outer housing means for admitting and discharging air from between said outer and inner housing means; and fan means for forcing the discharge of air from between said outer and inner housing means.

3. The system of claim 1, wherein said support means includes plate means vertically movable in said inner housing means; and bracket means on said plate means for mounting a sample on said plate means for movement therewith, permitting changing of the position of the sample relative to said camera means in the isothermal chamber.

4. The system of claim 1, wherein said support means includes frame means vertically movable in said inner housing means for supporting a sample in the isothermal chamber, said camera means being located in a top wall of said outer housing means and extending into the top of said inner housing means.

5. The system of claim 4, including slide means slidably supporting said frame means in said inner housing means; and drive means for moving said frame means relative to said camera means.

6. The system of claim 5, wherein said drive means includes internally threaded sleeve means on said frame means; threaded rod means extending through and engaging said sleeve means; and reversible motor means for rotating said rod means, whereby said sleeve means and said frame means are caused to move in said isothermal chamber relative to said camera means.

7. The system of claim 1, wherein said sensor means includes first thermocouple means in said isothermal chamber connected to said computer means and adapted to be connected to a sample for generating signals indicative of sample temperature; and second thermocouple means in said isothermal chamber for monitoring the ambient temperature in said chamber and for generating signals indicative of said ambient temperature.

* * * * *